United States Patent
Pandey et al.

(10) Patent No.: US 6,956,039 B2
(45) Date of Patent: Oct. 18, 2005

(54) NITROGENOUS HETEROCYLIC COMPOUNDS

(75) Inventors: Anjali Pandey, Fremont, CA (US); Robert M. Scarborough, Half Moon Bay, CA (US); Kenji Matsuno, Tokyo (JP); Michio Ichimura, Tokyo (JP); Yuji Nomoto, Shizuoka (JP); Shinichi Ide, Tokyo (JP); Eiji Tsukuda, Tokyo (JP); Junko Sasaki, Akita (JP); Shoji Oda, Tokyo (JP)

(73) Assignees: Millennium Pharmaceuticals, Inc., Cambridge, MA (US); Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 10/344,737

(22) PCT Filed: Aug. 17, 2001

(86) PCT No.: PCT/US01/41751
§ 371 (c)(1),
(2), (4) Date: Mar. 18, 2004

(87) PCT Pub. No.: WO02/16362
PCT Pub. Date: Feb. 28, 2002

(65) Prior Publication Data
US 2004/0186110 A1 Sep. 23, 2004

Related U.S. Application Data

(60) Provisional application No. 60/226,089, filed on Aug. 18, 2000.

(51) Int. Cl.⁷ .............................................. C07D 487/00
(52) U.S. Cl. .................. 514/252.17; 544/284
(58) Field of Search ..................... 514/252.17; 544/284

(56) References Cited

U.S. PATENT DOCUMENTS

| | | | |
|---|---|---|---|
| 6,169,088 B1 | 1/2001 | Matsuno et al. | 514/252.16 |
| 6,207,667 B1 | 3/2001 | Matsuno et al. | 514/252.13 |
| 6,423,716 B1 * | 7/2002 | Matsuno et al. | 514/252.02 |
| 6,472,391 B2 * | 10/2002 | Matsuno et al. | 514/243 |
| 6,750,218 B2 * | 6/2004 | Matsuno et al. | 514/248 |
| 2002/0068734 A1 | 6/2002 | Matsuno et al. | 514/243 |

FOREIGN PATENT DOCUMENTS

| | | |
|---|---|---|
| EP | 0 882 717 A | 12/1998 |
| EP | 1 067 123 A | 1/2001 |
| WO | 99-51582 * | 10/1999 |
| WO | WO 02/16351 A2 | 2/2002 |
| WO | WO 02/16360 A2 | 2/2002 |
| WO | WO 02/16361 A2 | 2/2002 |
| WO | WO 02/072578 A2 | 9/2002 |

OTHER PUBLICATIONS

Agrawal, Vijai et al.: "Antiparasitic agents, Part VI: Synthesis of 7–chloro–4–(4–substituted–phenylanino)– and 7–chloro–4–(4–substituted–piperazin–1–yl)quinolines as potential antiparasitic agents" Indian J. Chem., Sect. B (1987), 26(B)6, pp. 550–555.

* cited by examiner

Primary Examiner—James O. Wilson
Assistant Examiner—Tamthom N. Truong
(74) Attorney, Agent, or Firm—Townsend and Townsend and Crew LLP

(57) ABSTRACT

The present invention relates to nitrogen-containing heterocyclic compounds and pharmaceutically acceptable salts thereof which have inhibitory activity on the phosphorylation of kinases, which inhibits the activity of such kinases. The invention is also related to a method of inhibiting kinases and treating disease states in a mammal by inhibiting the phosphorylation of kinases. In a particular aspect the present invention provides nitrogen-containing heterocyclic compounds and pharmaceutically acceptable salts thereof which inhibit phosphorylation of a PDGF receptor to hinder abnormal cell growth and cell wandering, and a method for preventing or treating cell-proliferative diseases such as arteriosclerosis, vascular reobstruction, cancer and glomerulosclerosis.

10 Claims, No Drawings

NITROGENOUS HETEROCYLIC COMPOUNDS

TECHNICAL FIELD

The present invention relates to nitrogen-containing heterocyclic compounds and pharmaceutically acceptable salts thereof which have inhibitory activity on the phosphorylation of kinases, which inhibits the activity of such kinases. The invention is also related to a method of inhibiting kinases and treating disease states in a mammal by inhibiting the phosphorylation of kinases.

BACKGROUND ART

PDGF (platelet-derived growth factor) is known to act as an aggravating factor for cell-proliferative diseases such as arteriosclerosis, vascular reobstruction after percutaneous coronary angioplasty and bypass operation, cancer, glomerulonephritis, glomerulosclerosis, psoriasis and articular rheumatism [Cell, 46, 155–169 (1986); Science, 253, 1129–1132 (1991); Nippon Rinsho (Japanese J. of Clinical Medicine), 50, 3038–3045 (1992); Nephrol Dial Transplant, 10, 787–795 (1995); Kidney International, 43 (Suppl. 39), 86–89 (1993); Journal of Rheumatology, 21, 1507–1511 (1994); Scandinavian Journal of Immunology, 27, 285–294 (1988), etc.].

As for quinazoline derivatives which are useful as drugs, N,N-dimethyl-4-(6,7-dimethoxy-4-quinazolinyl)-1-piperazine carboxamide is described as a bronchodilator in South African Patent No. 67 06512 (1968). Dimethoxyquinazoline derivatives are described as inhibitors of phosphorylation of epidermal growth factor (EGF) receptor in Japanese Published Unexamined Patent Application No. 208911/93 and WO 96/09294. Quinoline derivatives having benzodiazepin receptor agonist activity are described in Pharmacology Biochemistry and Behavior, 53, 87–97 (1996) and European Journal of Medicinal Chemistry, 31, 417–425 (1996), and quinoline derivatives which are useful as anti-parasite agents are described in Indian Journal of Chemistry, 26B, 550–555 (1987).

Inhibitors of phosphorylation of PDGF receptor so far known include bismono- and bicyclic aryl compounds and heteroaryl compounds (WO 92/20642), quinoxaline derivatives [Cancer Research, 54, 6106 (1994)], pyrimidine derivatives (Japanese Published Unexamined Patent Application No. 87834/94) and dimethoxyquinoline derivatives [Abstracts of the 16th Annual Meeting of the Pharmaceutical Society of Japan (Kanazawa) (1996), 2, p. 275, 29(C2) 15-2].

DISCLOSURE OF THE INVENTION

An object of the present invention is to provide nitrogen-containing heterocyclic compounds and pharmaceutically acceptable salts thereof which have inhibitory activity on the phosphorylation of kinases, which inhibits the activity of the kinases. Particularly, important kinase inhibition according to the invention is of receptor tyrosine kinases including platelet-derived growth factor (PDGF) receptor, Flt3, CSF-1R, epidermal growth factor receptor (EGRF), fibroblast growth factor (FGF), vascular endothelial growth factor receptor (VEGFR) and others. Another class of kinase inhibition according to the invention is inhibitory activity nonreceptor tyrosine kinases including src and abl, and the like. A third class of kinase inhibition according to the invention is inhibitory activity toward serine/threonine kinases, including such kinases as MAPK, MEK and cyclin dependent kinases (CDKs) that mediate cell prolifetation, AKT and CDK such that mediate cell survival and NIK that regulate inflammatory responses. Inhibition of such kinases can be used to treat diseases involving cell survival, proliferation and migration, including cardiovascular disease, such as arteriosclerosis and vascular reobstruction, cancer, glomerulosclerosis fibrotic diseases and inflammation, as well as the general treatment of cell-proliferative diseases.

In a preferred embodiment, the present invention provides compounds and pharmaceutically acceptable salts thereof which inhibit or prevent inhibition of phosphorylation of at least one PDGF receptor by at least one tyrosine kinase. Such PDGF receptor kinase inhibition can hinder abnormal cell growth and cell wandering, and thus such compounds are useful for the prevention or treatment of cell-proliferative diseases such as arteriosclerosis, vascular reobstruction, cancer and glomerulosclerosis.

The present invention relates to nitrogen-containing heterocyclic compounds represented by formula I as follows:

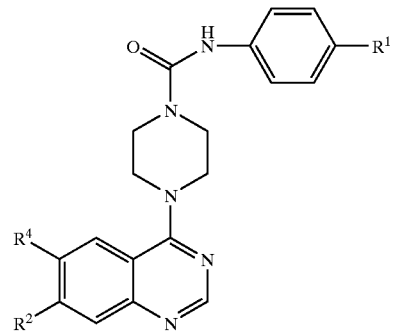

wherein
R$^1$ is a member selected from the group consisting of:
—CN, —O—C$_{1-8}$ alkyl that is a straight or branched chain, —O-phenyl, —O-naphthyl, —O-indolyl and —O-isoquinolinyl;
R$^2$ and R$^4$ are each independently a member selected from the group consisting of:
hydrogen, —O(—CH$_2$)—CH$_3$, —O—CH$_2$—CH=CH$_2$, —O—CH$_2$—C4CH and —O(—CH$_2$)$_n$—R$^3$; providing that one of the R$^2$ and R$^4$ groups is hydrogen and the remaining R$^2$ or R$^4$ group is other than hydrogen;
n is 1, 2 or 3;
R$^3$ is a member selected from the group consisting of:
—OH, —O—CH$_3$, —O—CH$_2$—CH$_3$, —NH$_2$, —N(—CH$_3$)$_2$, —NH(—CH$_2$-phenyl), —NH(-Phenyl), —CN

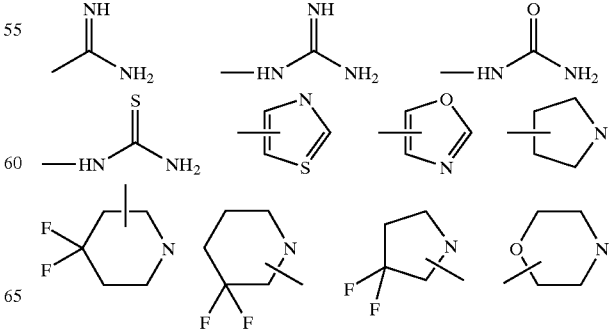

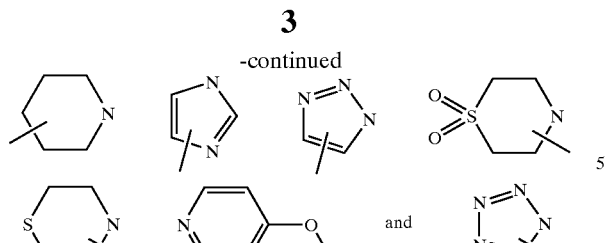

and all pharmaceutically acceptable isomers, salts, hydrates, solvates and prodrug derivatives thereof.

Particularly preferred compounds according to formula above are such compounds wherein $R^1$ is a member selected from the group consisting of CN, —O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy, 5-isoquinolyloxy, and position isomers and homologs thereof, and all pharmaceutically acceptable isomers, salts, hydrates, solvates and prodrug derivatives of such compounds.

The pharmaceutically acceptable salts of the compounds according to formula (I) include pharmaceutically acceptable acid addition salts, metal salts, ammonium salts, organic amine addition salts, amino acid addition salts, etc. Examples of the pharmaceutically acceptable acid addition salts of the compounds of formula (I) are inorganic acid addition salts such as hydrochloride, sulfate and phosphate, and organic acid addition salts such as acetate, maleate, fumarate, tartrate, citrate and methanesulfonate. Examples of the pharmaceutically acceptable metal salts are alkali metal salts such as sodium salt and potassium salt, alkaline earth metal salts such as magnesium salt and calcium salt, aluminum salt and zinc salt. Examples of the pharmaceutically acceptable ammonium salts are ammonium salt and tetramethyl ammonium salt. Examples of the pharmaceutically acceptable organic amine addition salts include heterocyclic amine salts such as morpholine and piperidine salts. Examples of the pharmaceutically acceptable amino acid addition salts are salts with lysine, glycine and phenylalanine.

In a preferred embodiment the invention provides compounds according to formula I(a) and formula I(b) as follows:

Formula I(a)

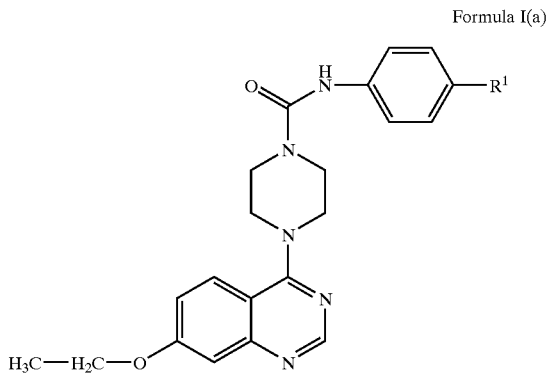

Formula I(b)

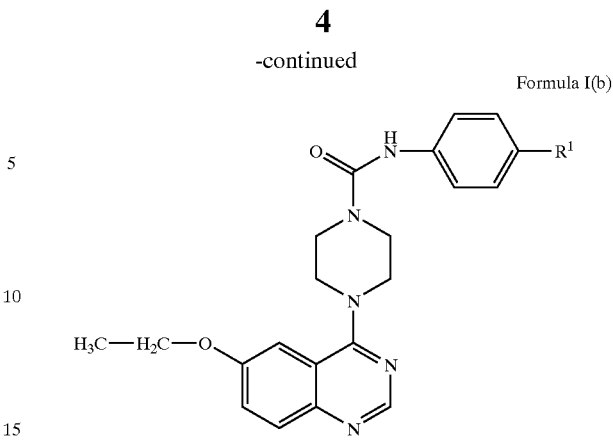

wherein $R^1$ is a member selected from the group consisting of:
—CN, —O—$C_{1-8}$ alkyl that is a straight or branched chain, —O-phenyl, —O-naphthyl, —O-indolyl and —O-isoquinolinyl;

and all pharmaceutically acceptable isomers, salts, hydrates, solvates and prodrug derivatives thereof.

In another preferred embodiment the invention provides compounds according to formula (Ic) and formula (Id) as follows:

Formula I(c)

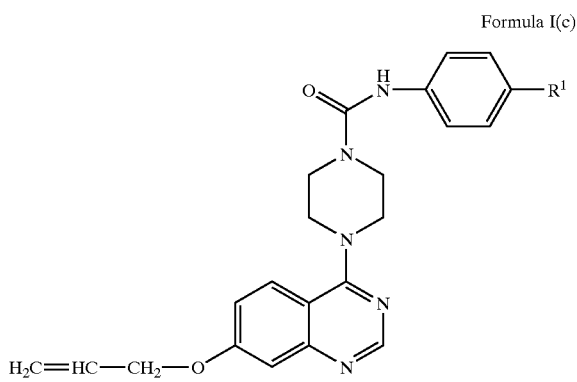

Formula I(d)

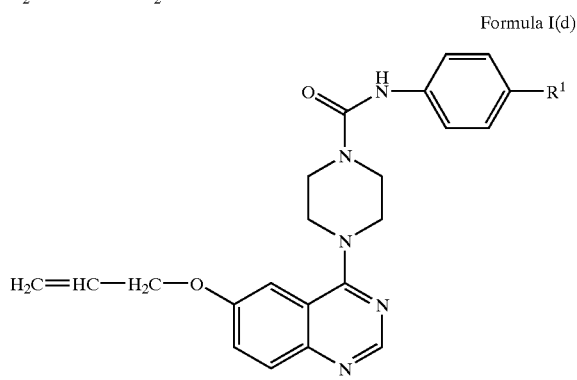

wherein $R^1$ is a member selected from the group consisting of:
—CN, —O—$C_{1-8}$ alkyl that is a straight or branched chain, —O-phenyl, —O-naphthyl, —O-indolyl and —O-isoquinolinyl;

and all pharmaceutically acceptable isomers, salts, hydrates, solvates and prodrug derivatives thereof.

In still another preferred embodiment the invention provides compounds according to formula I(e) and formula I(f) as follows:

Formula I(e)

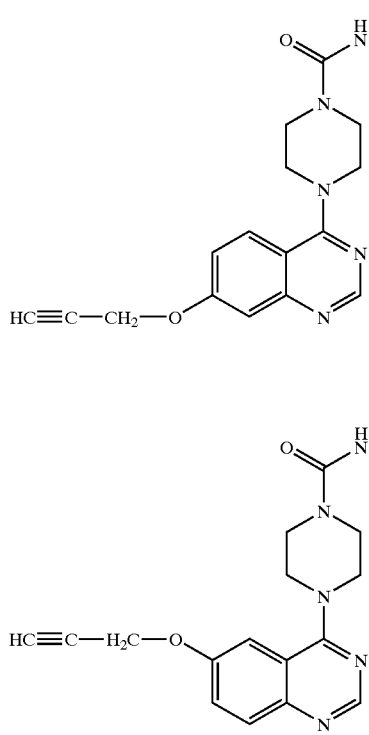

Formula I(f)

wherein

R$^1$ is a member selected from the group consisting of:
—CN, —O—C$_{1-8}$ alkyl that is a straight or branched chain, —O-phenyl, —O-naphthyl, —O-indolyl and —O-isoquinolinyl;

and all pharmaceutically acceptable isomers, salts, hydrates, solvates and prodrug derivatives thereof.

In yet another preferred embodiment the invention provides compounds according to formula I(g) and formula I(h) as follows:

Formula I(g)

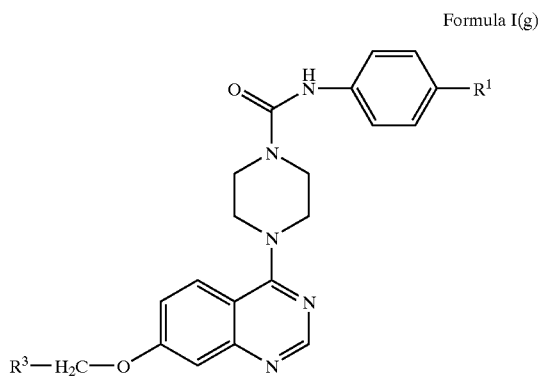

Formula I(h)

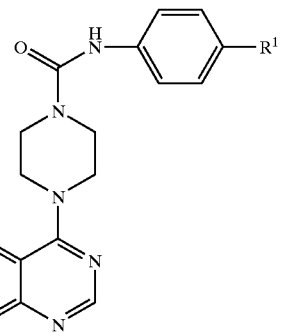

wherein

R$^1$ is a member selected from the group consisting of:
—CN, —O—C$_{1-8}$ alkyl that is a straight or branched chain, —O-phenyl, —O-naphthyl, —O-indolyl and —O-isoquinolinyl;

R$^3$ is a member selected from the group consisting of:
—OH, —O—CH$_3$, —O—CH$_2$—CH$_3$, —NH$_2$, —N(—CH$_3$)$_2$, —NH(—CH$_2$-phenyl), —NH(-Phenyl), —CN

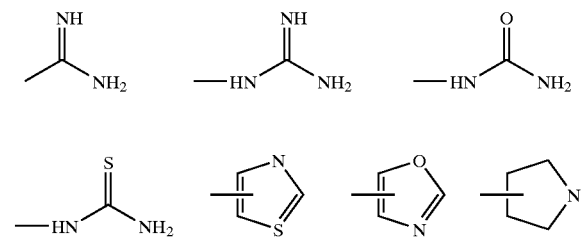

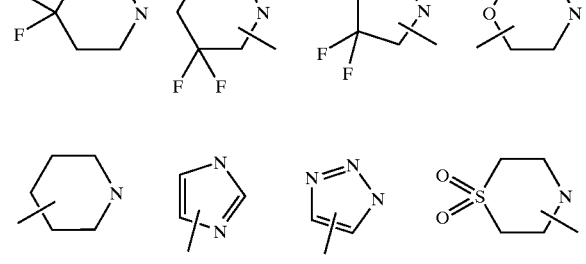

and all pharmaceutically acceptable isomers, salts, hydrates, solvates and prodrug derivatives thereof.

The pharmaceutically acceptable salts of the compounds according to formula (I) include pharmaceutically acceptable acid addition salts, metal salts, ammonium salts, organic amine addition salts, amino acid addition salts, etc.

The present invention is not limited by the above listed compounds. Analogs of the bicyclic compounds are contemplated.

Further, an especially preferred embodiment of the present invention is a compound selected from the group consisting of:

N-[4-(methylethoxy)phenyl]{4-[7-(2-morpholin-4-ylethoxy)quinazolin-4-yl]piperazinyl}carboxamide

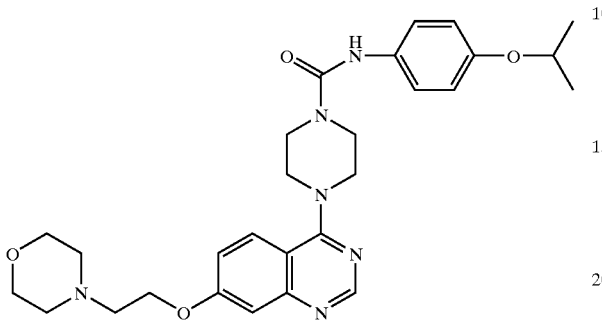

N-(4-cyanophenyl){4-[7-(2-morpholin-4-ylethoxy)quinazolin-4-yl]piperazinyl}carboxamide

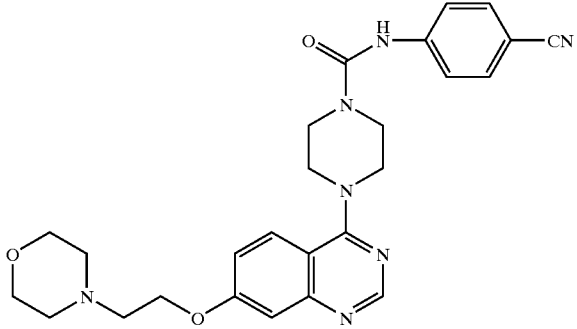

N-(4-cyanophenyl){4-[7-(2-pyrrolidinylethoxy)quinazolin-4-yl]piperazinyl}carboxamide

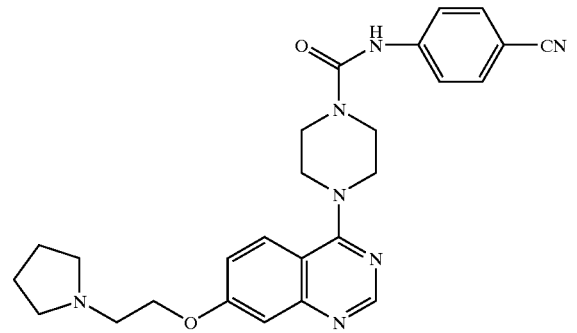

N-[4-(methylethoxy)phenyl]{4-[7-(2)pyrrolidinylethoxy)quinazolin-4-yl]piperazinyl}carboxamide

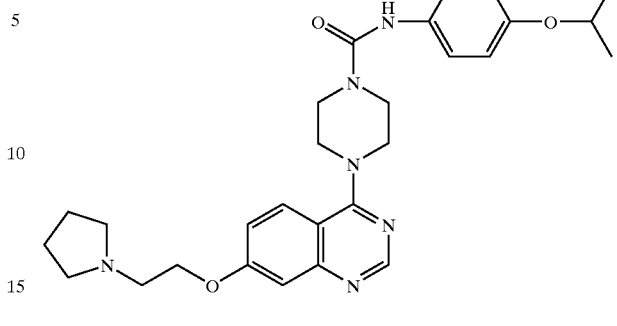

N-[4-(methylethoxy)phenyl]{4-[7-(2-piperidylethoxy)quinazolin-4-yl]piperazinyl}carboxamide

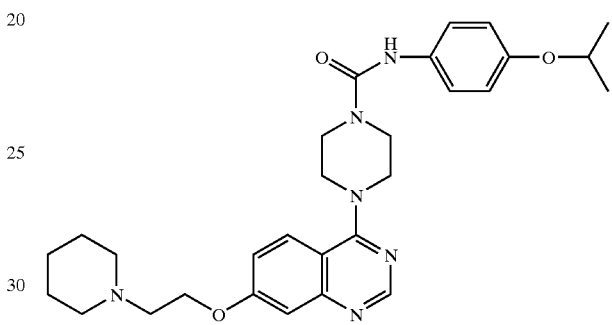

{4-[7-(2-methoxyethoxy)quinazolin-4-yl]piperazinyl}-N-[4-(methylethoxy)phenyl]carboxamide

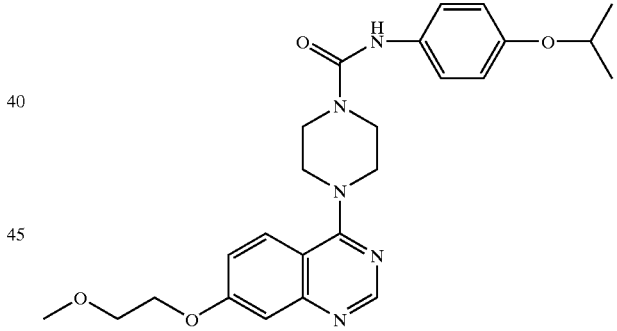

N-(4-cyanophenyl){4-[7-(2-methoxyethoxy)quinazolin-4-yl]piperazinyl}carboxamide

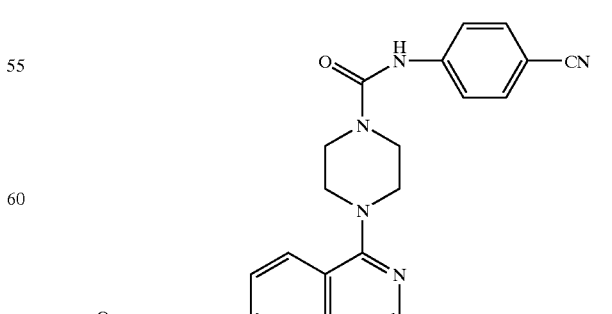

N-(4-cyanophenyl){4-[7-(2-piperidylethoxy)quinazoin-4-yl]piperazinyl}carboxamide

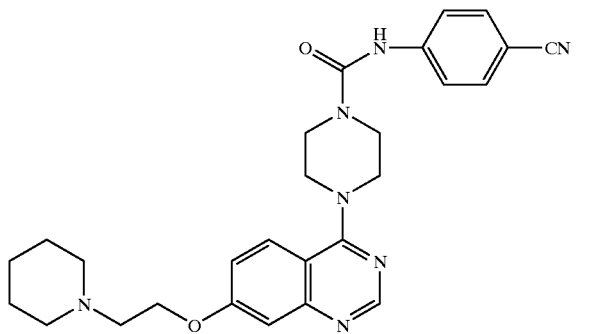

N-[4-(methylethoxy)phenyl]{4-[7-(3-piperidylpropoxy)quinazolin-4-yl]piperazinyl}carboxamide

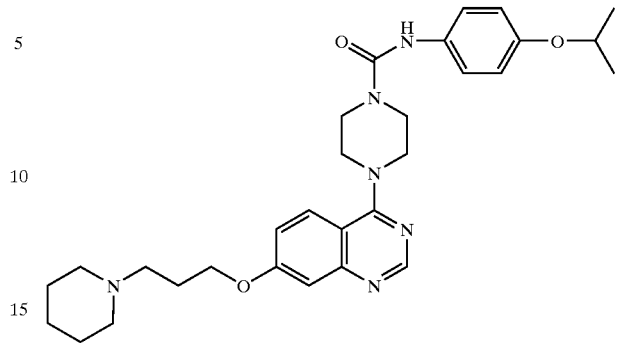

{4-[7-(2-methoxyethoxy)quinazolin-4-yl]piperazinyl}-N-(4-phenoxyphenyl)carboxamide

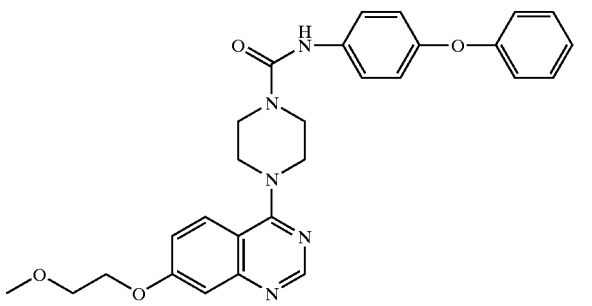

{4-[7-(2-methoxypropoxy)quinazolin-4-yl]piperazinyl}-N-(4-phenoxyphenyl)carboxamide

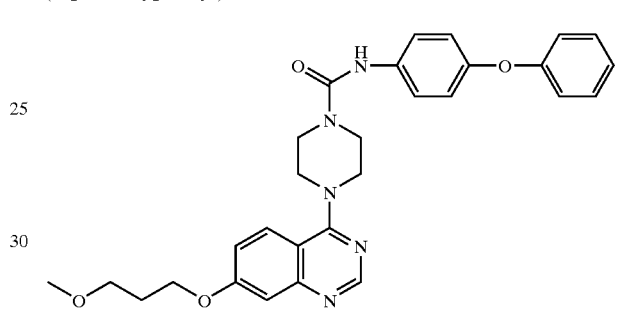

N-(4-indol-5-yloxyphenyl){4-[7-(2-methoxyethoxy)quinazolin-4-yl]piperazinyl}carboxamide

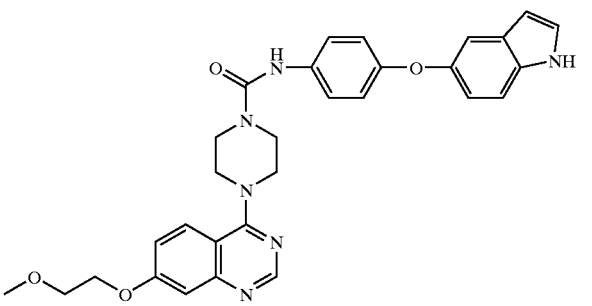

N-(4-indol-5-yloxyphenyl){4-[7-(2-methoxypropoxy)quinazolin-4-yl]piperazinyl}carboxamide

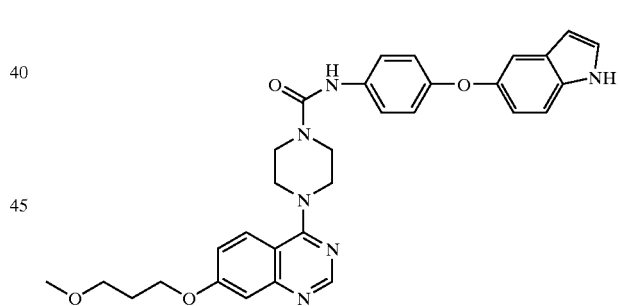

N-(4-(5-isoquinolyloxy)phenyl){4-[7-(2-methoxyethoxy)quinazolin-4-yl]piperazinyl}carboxamide

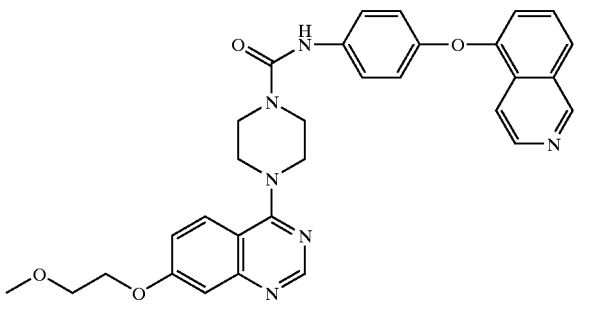

N-(4-(5-isoquinolyloxy)phenyl){4-[7-(2-methoxypropoxy)quinazolin-4-yl]piperazinyl}carboxamide

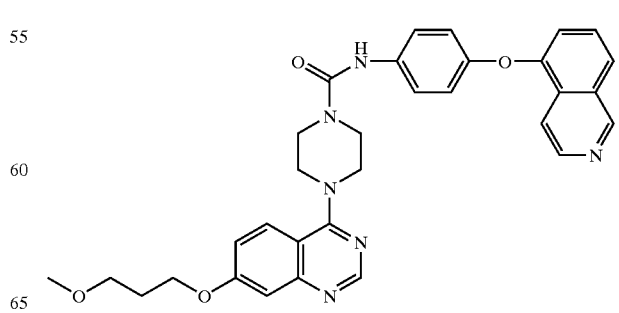

N-(4-cyanophenyl){4-[7-(3-piperidylpropoxy)quinazolin-4-yl]piperazinyl}carboxamide

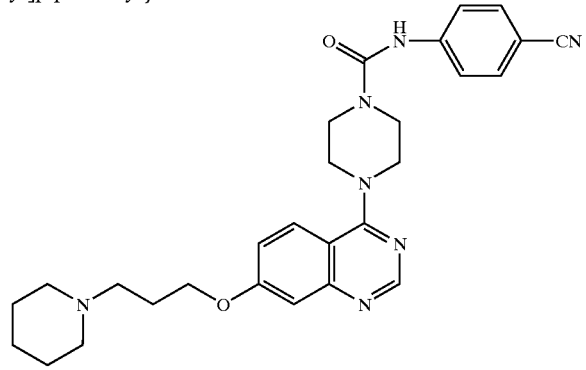

N-[4-(methylethoxy)phenyl]{4-[7-(3-morpholin-4-ylpropoxy)quinazolin-4-yl]piperazinyl}carboxamide

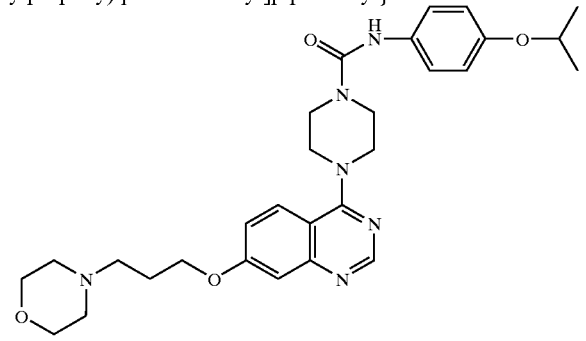

N-(4-cyanophenyl){4-[7-(3-morpholin-4-ylpropoxy)quinazolin-4-yl]piperazinyl}carboxamide

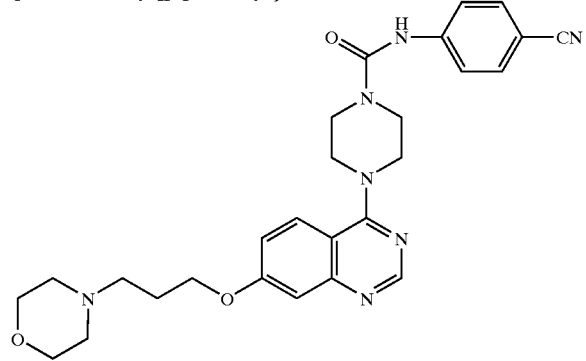

N-[4-(methylethoxy)phenyl]{4-[7-(3-pyrrolidinylpropoxy)quinazolin-4-yl]piperazinyl}carboxamide

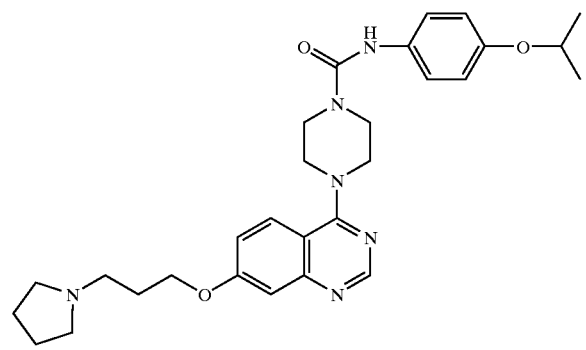

N-(4-cyanophenyl){4-[7-(3-pyrrolidinylpropoxy)quinazolin-4-yl]piperazinyl}carboxamide

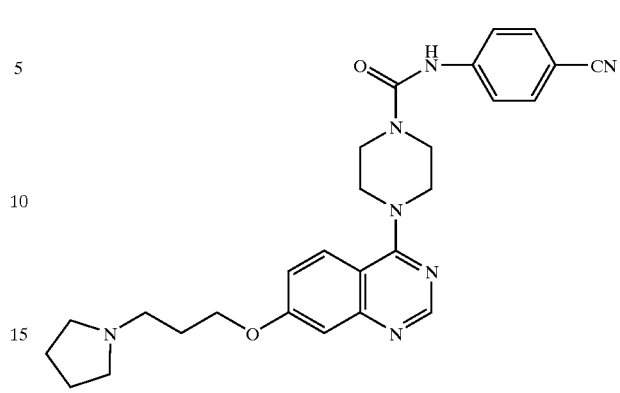

N-(4-cyanophenyl){4-[7-(3-methoxypropoxy)quinazolin-4-yl]piperazinyl}carboxamide

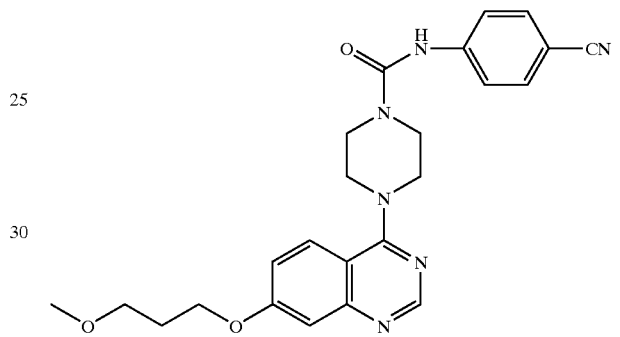

{4-[7-(3-methoxypropoxy)quinazolin-4-yl]piperazinyl}-N-[4-(methylethoxy)phenyl]carboxamide

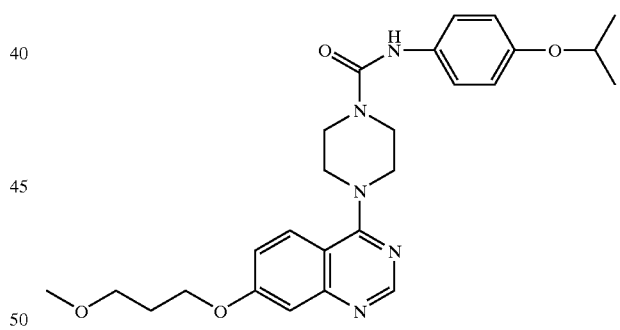

and all pharmaceutically acceptable isomers, salts, hydrates, solvates and prodrug derivatives thereof.

The compounds may be prepared using methods and procedures as generally described in WO 98/14431 published Sep. 12, 1998, which is incorporated herein by reference. Starting materials may be made or obtained as described therein as well.

Leaving groups such as halogen, lower alkoxy, lower alkylthio, lower alkylsulfonyloxy, arylsulfonyloxy, etc, may be utilized when necessary except for the reaction point, followed by deprotection. Suitable amino protective groups are, for example, those described in T. W. Greene, Protective Groups in Organic Synthesis, John Wiley & Sons Inc. (1981), etc., such as ethoxycarbonyl, t-butoxycarbonyl, acetyl and benzyl. The protective groups can be introduced and eliminated according to conventional methods used in organic synthetic chemistry [e.g., T. W. Greene, Protective Groups in Organic Synthesis, John Wiley & Sons Inc. (1981)].

In such processes, if the defined groups change under the conditions of the working method or are not appropriate for carrying out the method, the desired compound can be obtained by using the methods for introducing and eliminating protective groups which are conventionally used in organic synthetic chemistry [e.g., T. W. Greene, Protective Groups in Organic Synthesis, John Wiley & Sons Inc. (1981)], etc. Conversion of functional groups contained in the substituents can be carried out by known methods [e.g., R. C. Larock, Comprehensive Organic Transformations (1989)] in addition to the above-described processes, and some of the active compounds of formula I may be utilized as intermediates for further synthesizing novel derivatives according to formula I.

The intermediates and the desired compounds in the processes described above can be isolated and purified by purification methods conventionally used in organic synthetic chemistry, for example, neutralization, filtration, extraction, washing, drying, concentration, recrystallization, and various kinds of chromatography. The intermediates may be subjected to the subsequent reaction without purification.

There may be tautomers for some formula I, and the present invention covers all possible isomers including tautomers and mixtures thereof. Where chiral carbons lend themselves to two different enantiomers, both enantiomers are contemplated as well as procedures for separating the two enantiomers.

In the case where a salt of a compound of formula I is desired and the compound is produced in the form of the desired salt, it can be subjected to purification as such. In the case where a compound of formula I is produced in the free state and its salt is desired, the compound of formula I is dissolved or suspended in a suitable organic solvent, followed by addition of an acid or a base to form a salt.

The following non-limiting reaction Schemes I, II and III illustrate preferred embodiments of the invention with respect to making compounds according to the invention.

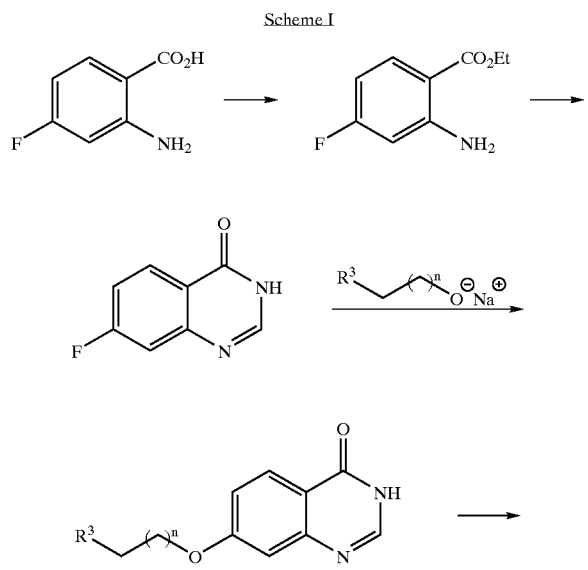

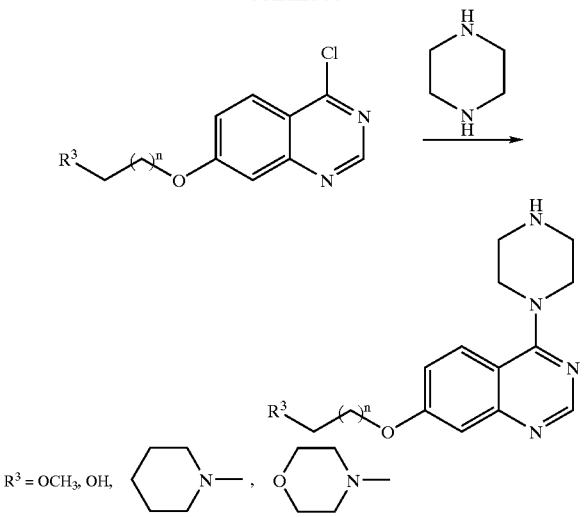

Scheme I describes the synthesis 7-(2-methoxyethoxy)-4-piperazinylquinazoline a key intermediate that will be utilized in the synthesis of various targets as described in Scheme II. The 2-amino-4-fluorobenzoic acid is esterified followed by cyclization with formamide at elevated temperature to afford 7-fluoro-4-quinazolinone. The 7-fluoro group is displaced with several alkoxides generated by treating with NaH in DMF at 100° C. The 7-alkoxy-4-quinazolinone is intermediate is converted to 7-alkoxy-4-chloroquinazoline with thionyl chloride. The key intermediate I was obtained by treating 7-alkoxysubsti-tuted-4-Cl-quinazoline with piperazine in an appropriate solvent, such as isopropanol, acetonitrile, or THF at room or reflux temperature for 1–6 h in presence of base triethylamine or pyridine.

This illustrated Scheme II provides the synthesis of various substituted urea from the intermediate obtained in Scheme I, or by other procedures. The reaction of intermediate I with various isocyanates afforded the final urea compounds. In cases where the isocyanates are not conunercially available, the piperazine intermediate is treated with phosgene to give carbamoyl chloride intermediate followed by reaction with various substituted anilines. The piperazine intermediate can also be treated with p-nitrophenyl chloroformate to afford nitrophenyl carbamate intermediate that can be treated with various anilines to afford the desired ureas.

If the urea compound has a terminal $NH_2$ group (or one or more of the hydrogen atoms on this amino group is replaced by a displaceable substituent), then this compound may be utilized an intermediate compound with which to produce a urea compound terminated with a —NH-phenyl-$R^1$ groups. Alternatively, if the a different $R^1$ group is desired on the phenyl group, a replaceable para position leaving group phenyl substituent may be displaced after coupling to provide the particular $R^1$ substituent as described for formula I, above.

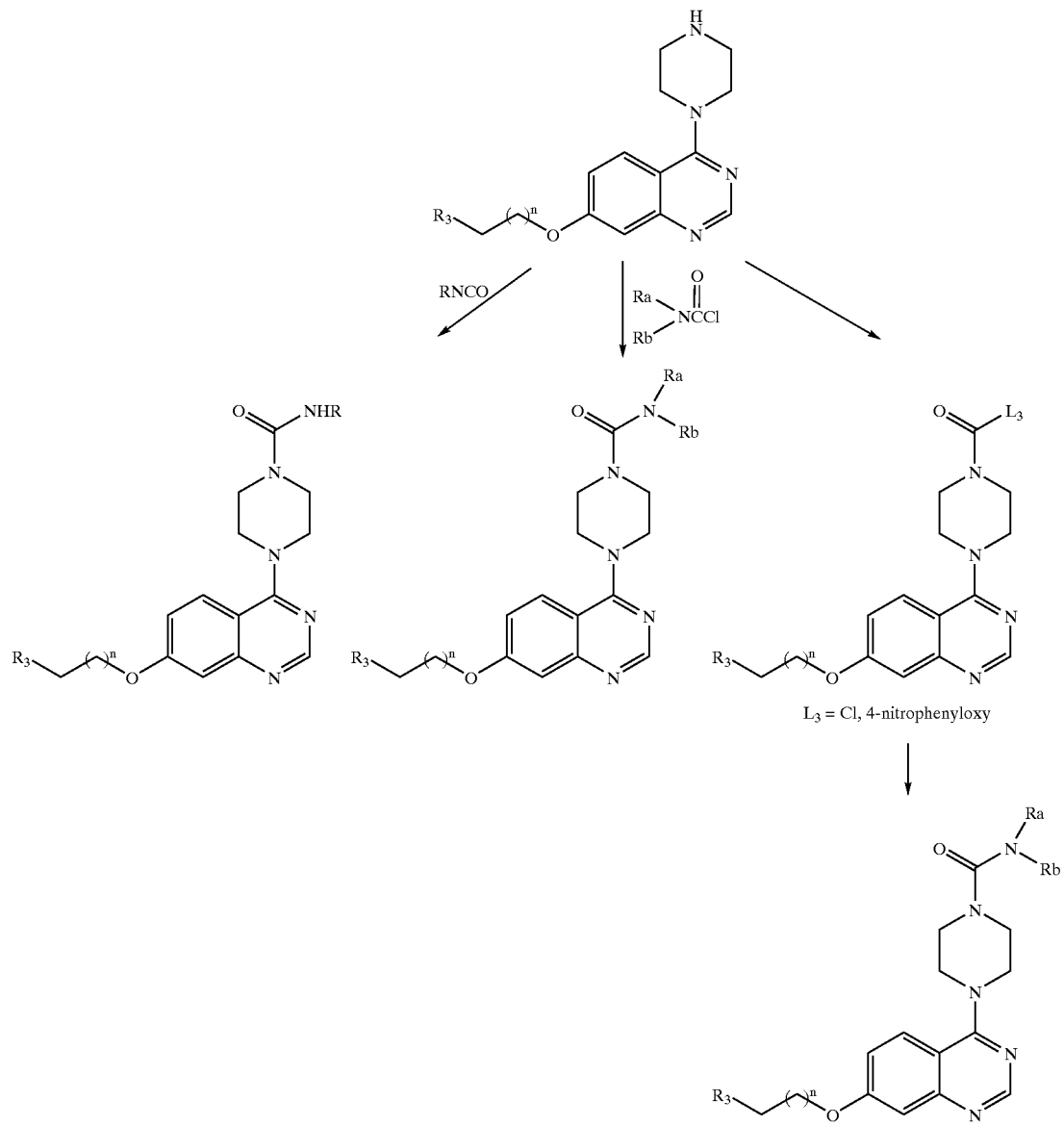
Scheme III describes the synthesis of 6-(2-methoxyethoxy)-4-piperazinylquinazoline as a key intermediate that will be utilized in the synthesis of various positional isomer targets.
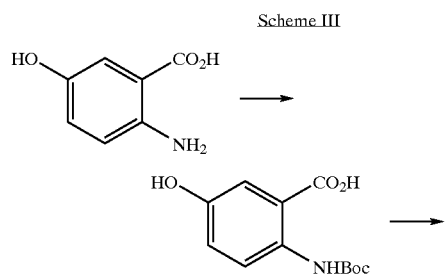
-continued
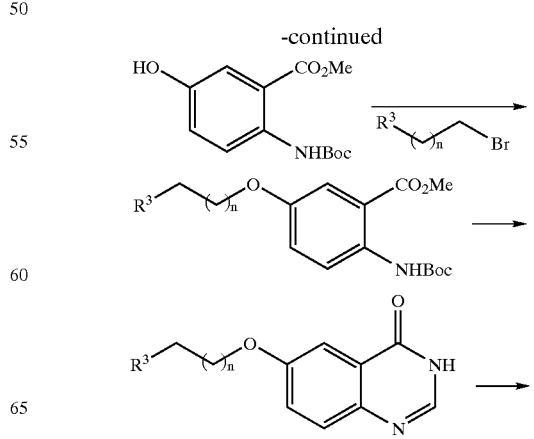

-continued

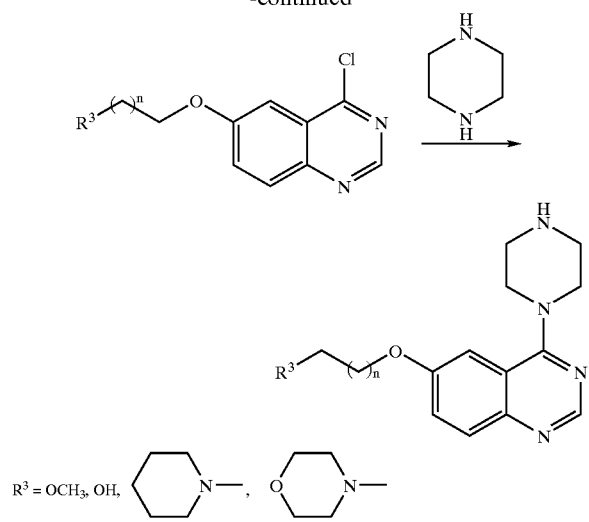

R³ = OCH₃, OH, 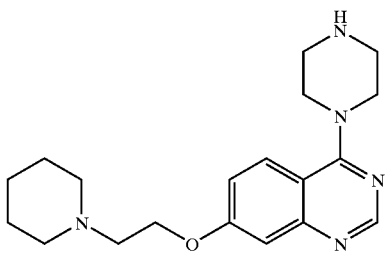

Such procedures for producing the claimed compounds are merely an illustration of a preferred aspect of the invention. Other procedures and adaptations will be apparent to one of ordinary skill in the art upon views these reaction schemes and the structures of the compounds according to the invention. Such procedures are deemed to be within the scope of the present invention.

Also, the compounds of formula I and pharmaceutically acceptable salts thereof may exist in the form of adducts with water (hydrates) or various solvents, which are also within the scope of the present invention.

The following non-limiting examples are provided to better illustrate the present invention.

EXAMPLE 1

The intermediate 4-piperazinyl-7-(2-piperidylethoxy) quinazoline was prepared using the procedures as generally described in Scheme 1 as follows:

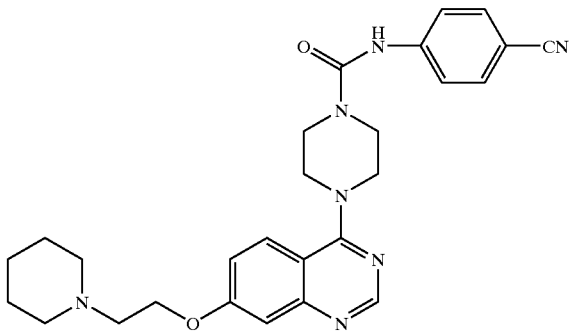

Step A To the ethanol solution (15 mL) of 2-amino-4-fluorobenzoic acid (840 mg, 5.41 mmol) was added thionyl chloride (1.18 mL, 16.23 mmol) and the resulting suspension was refluxed overnight. The solvent was evaporated to the residue added EtOAc, washed with 10% NaOH solution, dried, filtered and evaporated to afford desired ethyl ester as a solid 981 mg, 82%). MS (ES) 184(M+H)

Step B: To the formamide (6 mL) solution of ethyl-2-amino-4-fluorobenzoate (811 mg, 4.43 mmol) added ammonium formate (0.450 g, 7.14 mmol) and the reaction mixture was heated at 140° C. overnight. After cooling added water and ethyl acetate. The layers were separated, the EtOAc layer was dried, filtered and evaporated to give desired quinazolinone (1 g, quantitative). MS (ES) 165 (M+H)

Step C: To the DMF solution (3 mL) of 1-piperidineethanol (0.689 mL, 5.18 mmol) at 0° C. added sodium hydride (0.518 g, 12.95 mmol) and the mixture was stirred for 30 min. To this cold solution added DMF solution (3 mL) of intermediate quinazolinone (0.284 g, 1.73 mmol, from Step B) and the mixture was heated at 75° C. overnight. The solvent was evaporated and the residue purified by RP-HPLC to afford desired product as a creamy solid (0.459 g, 97%)

Step D: A mixture of 7-(2-piperidylethoxy)-4-quinazolinone (0.459 g, 1.68 mmol), from Step C) and POCl₃ (5 mL) was heated at 75° C. overnight. After cooling excess POCl₃ was removed by evaporation and the residue azeotroped with toluene to afford intermediate, 4-chloro-7-(2-piperidylethoxy)quinazoline (600 mg, 95%)

Step E: To the isopropanol solution (10 mL) of 4-chloroquinazoline (0.615 g, 2.11 mmol, from Step D) added piperazine (0.727 g, 8.44 mmol) and heated the reaction for 4 h at 100° C. The solvent was evaporated and the residue purified by RP-HPLC to afford 4-piperazinyl-7-(2-piperidylethoxy)quinazoline as a white solid (0.630 g, 87%).

EXAMPLE 2

Preparation of N-(4-cyanophenyl){4-[7-(2-piperidylethoxy)quinazolin-4-yl]piperazinyl}-carboxamide

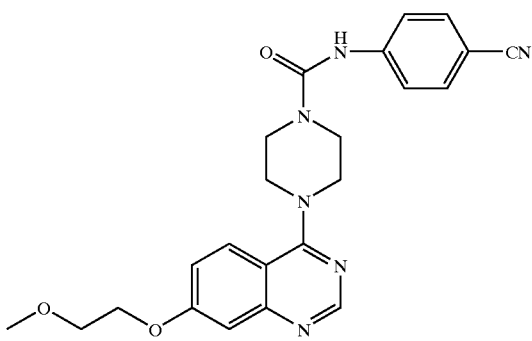

To DMF solution (2 mL) of 4-piperazinyl-7-(2-piperidylethoxy)quinazoline (from Example 1, Step E, 0.287 g, 0.84 mmol) added DMF solution (2 mL) of 4-cyanophenylisocyanate (0.181 g, 1.26 mmol) and the reaction was stirred at room temperature overnight. The solvent was evaporated and residue purified by RP-EHLC to afford desired product N-(4-cyanophenyl){4-[7-(2-piperidylethoxy)quinazolin-4-yl]piperazinyl}carboxamide as a white solid (200 mg, 50%). MS (ES) 487(M+H)

EXAMPLE 3–4

N-(4-cyanophenyl){4-[7-(2-methoxyethoxy)quinazolin-4-yl]piperazinyl}-carboxamide was prepared using the procedures as described above in Example 1 and 2 except that 2-methoxyethanol was used instead of 1-piperidineethanol as an alkoxide anion, to provide the title compound.

The pharmacological activities of the compounds of the present invention are obtained by following the test example procedures as follows, for example.

Biological Test Assay Type 1
Inhibitory Effect on Compounds on Autophosphorylation of Platelet Derived Growth Factor β-PDGF Receptor
(1) HR5 Phosphorylation Assay The HR5 cell line is a cell line of CHO cells engineered to overexpress human β-PDGFR, which cell line is available from the ATCC. The expression level of β-PDGFR in HR5 cells is around $5\times10^4$ receptor per cell. For the phosphorylation assay according to the invention, HR5 cells were grown to confluency in 96-well microtiter plates under standard tissue culture conditions, followed by serum-starvation for 16 hours. Quiescent cells were incubated at 37° C. without or with increasing concentrations of the test compound (0.01–30 uM) for 30 minutes followed by the addition of 8 nM PDGF BB for 10 minutes. Cells were lysed in 100 mM Tris, pH7.5, 750 mM NaCl, 0.5% Triton X-100, 10 mM sodium pyrophosphate, 50 mM NaF, 10 ug/ml aprotinin, 10 ug/ml leupeptin, 1 mM phenylmethylsulfonyl fluoride, 1 mM sodium vanadate, and the lysate was cleared by centrifugation at 15,000×g for 5 minutes. Clarified lysates were transferred into a second microtiter plate in which the wells were previously coated with 500 ng/well of 1B5B11 anti-β-PDGFR mAb, and then incubated for two hours at room temperature. After washing three times with binding buffer (0.3% gelatin, 25 mM Hepes pH 7.5, 100 mM NaCl, 0.01% Tween-20), 250 ng/ml of rabbit polyclonal anti-phosphotyrosine antibody (Transduction Laboratory) was added and plates were incubated at 37° C. for 60 minutes. Subsequently, each well was washed three times with binding buffer and incubated with 1 ug/ml of horse radish peroxidase-conjugated anti-rabbit antibody (Boehringer Mannheim) at 37° C. for 60 minutes. Wells were washed prior to adding ABTS (Sigma), and the rate of substrate formation was monitored at 650 nm. The assay results are reported as $IC_{50}$ (expressed as the concentration of a compound according to the invention that inhibits the PDGF receptor phosphorylation by 50%) as compared to control cells that are not exposed to a compound according to the invention.

Examples of such $IC_{50}$ test results in the HR5 assay for compounds according to the invention are set forth below in Table 1.

(2) MG63 Phosphorylation Assay

The MG63 cell line is a human osteosarcoma tumor cell line available from the ATCC. This assay is for measuring endogenous β-PDGFR phosphorylation in MG63 cells. The assay conditions are the same as those described at for HR5 cell, except that PDGF-BB stimulation is provided in the presence or absence of 45% human plasma. The HR5 assay results are reported as an $IC_{50}$ (expressed as the concentration of a compound according to the invention that inhibits the PDGF receptor phosphorylation by 50%) as compared to control cells that are not exposed to a compound according to the invention.

Examples of such $IC_{50}$ test results in the MG63 assay for compounds according to the invention are set forth below in Table 1.

The assay results for Compound Examples 1 and 2 are set forth in Table 1 below.

TABLE 1

| Example Compound | MG63 w/human plasma $IC_{50}$ (µM) | HR5 $IC_{50}$ (µM) |
|---|---|---|
| Example 1 | 0.103 | 0.150 |
| Example 2 | 3.56 | 2.27 |

Biological Test Assay Type 2
Growth Inhibition Against Smooth Muscle cells

Vascular smooth muscle cells are isolated from a pig aorta by explanation and used for the test. The cells are put into wells of a 96-well plate (8000 cells/well) and cultured in Dulbeccois modified Eagle's medium (DMEM; Nissui Pharmaceutical Co., Ltd.) containing 10% fetal bovine serum (FBS; Hyclone) for 4 days. Then, the cells are further cultured in DMEM containing 0.1% FBS for 3 days, and are synchronized at the cell growth stationary phase.

To each well is added DMEM containing 0.1% FBS and a test sample at a varied concentration, and the cell growth is brought about by PDGF-BB (SIGMA, final concentration: 20 ng/ml). After culturing for 3 days, the cell growth is measured using a cell growth assay kit (Boehringer Mannheim) according to the XTT method [J. Immunol. Methods, 142, 257–265 (1991)], and the cell growth score is calculated by the following equation.

Cell growth score=$100\times\{1-(M-PO)/(P100-PO)\}$ wherein P100=absorbance by XTT reagent when stimulated by PDGF-BB; PO=absorbance by XTT reagent when not stimulated by PDGF-BB, and M=absorbance by XTT reagent after addition of a sample when stimulated by PDGF-BB.

The test result is expressed as the concentration of a test compound which inhibits the cell growth by 50% ($IC_{50}$).

Biological Test Assay Type 3
Inhibitory Effect on Hypertrophy of Vascular Intima Male SD rats (weight: 375–445 g, Charles River, golden standard) are anesthetized with sodium pentobarbital (50 mg/kg, i.p.), and then the neck of each animal is incised by the median incision, followed by retrograde insertion of a balloon catheter (2F, Edwards Laboratories) into the left external carotid. After the above treatment is repeated seven times, the catheter is pulled out, the left external carotid is ligated, and the wound is sutured. A test compound is suspended in a 0.5% solution of Tween 80 in an aqueous solution of sodium chloride to a concentration of 20 mg/ml in the case of intraperitoneal administration and in a 0.5% solution of methyl cellulose 400 to a concentration of 6 mg/ml in the case of oral administration. The suspension is administered once a day in the case of intraperitoneal administration and once or twice a day in the case of oral administration for a period of 15 days starting on the day before the balloon injury. On the 14th day after the balloon injury, the animal is killed and its left carotid is extirpated. The tissues are fixed with formalin, wrapped in paraffin and sliced, followed by Elastica Wangeeson staining. The area of the cross section of the vascular tissues (intima and media) is measured with an image analyzer (Luzex F, NIRECO) and the intima/media area ratio (I/M) is regarded as the degree of hypertrophy of the vascular intima.

From the results obtained, it is apparent when the hypertrophy of vascular intima is significantly inhibited by administration of the compounds of the present invention.

Biological Test Assay Type 4
Evaluation by the Use of a Rat Adjuvant Arthritis Model Dead cells of Mycobacterium bacterium (Difco Laboratories Inc.) are disrupted in agate mortar and suspended in liquid paraffin to the final concentration of 6.6 mg/ml, followed by sterilization with high pressure steam. Then, 100 ml of the suspension is subcutaneously injected into the right hind foot pad of each animal of groups of female 8-weeks-old Lewis rats (Charles River Japan) (6 animals/group) to induce adjuvant arthritis. A test compound is suspended in a 0.5% solution of methyl cellulose to the final concentration of 3 mg/ml, and from just before the induction of arthritis, the suspension is orally administered in an amount of 100 ml/100 g of the body weight once a day, 5 days a week. To a control group is administered a 0.5% solution of methyl cellulose. A normal group is given no adjuvant treatment or test compound administration. The administration of the test compound is continued till the 18th day after the adjuvant treatment. On the 17th day, the number of leukocytes in peripheral blood are counted, and on the 18th day, all the blood is collected, followed by dissection.

The change in body weight with the passage of time, the change of edema in hind foot with the passage of time, the weight of spleen and thymus, the number of leukocytes in peripheral blood, the hydroxyproline content of urine, the glucosaminoglycan content of urine, the SH concentration in serum, the concentration of nitrogen monoxide in serum and the concentration of mucoprotein in serum are measured and evaluated. The volume of each of both hind feet are measured using a rat's hind foot edema measurement device (TK-101, Unicom). The number of leukocytes in peripheral blood are counted using an automatic multichannel blood cell counter (Sysmex K-2000, Toa Iyo Denshi Co., Ltd.). The hydroxyproline content of urine is measured according to the method described in Ikeda, et al., Annual Report of Tokyo Metropolitan Research Laboratories P. H., 36, 277 (1985), and the glucosaminoglycan content is measured according to the method described in Moriyama, et al., Hinyo Kiyo, 40, 565 (1994) and Klompmakers, et al., Analytical Biochemistry, 153, 80 (1986). The SH concentration in serum is measured according to the method described in Miesel, et al., Inflomation, 17, 595 (1993), and the concentration of nitrogen monoxide is measured according to the method ofTracey, et al., Journal of Pharmacology & Experimental Therapeutics, 272, 1011 (1995). The concentration of mucoprotein is measured using Aspro GP Kit (Otsuka Pharmaceutical Co., Ltd.). The percentage inhibition for each indication is calculated according to the following equation.

% Inhibition={(Control group−Compound-administered group)/(Control group−Normal group)}×100.

From the results obtain from such assays, it is apparent when the compound according to the invention inhibits the occurrence of adjuvant arthritis.

Biological Test Assay Type 5

Activity on a Mesangial Proliferative Glomerulonephritis Model

Anti-rat Thy-1.1 monoclonal antibody OX-7 (Sedaren) is administered to male Wister-Kyoto rats (Charles River Japan, 160 g, 6 animals/group) in an amount of 1.0 mg/kg by intravenous adminstration through the tail vein. A test compound is suspended in a 0.5% solution of methylcellulose and the resulting suspension is administered to each of the rats twice a day for a period of 7 days starting on the day before the administration of OX-7. On the 7th day after the OX-7 administration, when mesangial cell growth and extracellular matrix hypertrophy become prominent, the left kidney of each rat is extirpated, fixed with 20% buffered formalin for 6 hours and wrapped in paraffin, followed by slicing. The obtained pieces are subjected to immune tissue staining using antibody PC10 (DAKO) against an intranuclear antigen of proliferative cells. After comparative staining with Methyl Green staining solution using diaminobenzidine as a color developer, the paraffin pieces are enclosed. Half of the glomeruli in a kidney piece are observed and the number of the cells in one glomerulus which are positive to the intranuclear antigen of proliferative cells are calculated. The test for the significance of difference is carried out by the Wilcoxon test.

From such results, it is apparent when the compounds according to the present invention show alleviating activity on mesangial proliferative glomerulonephritis.

The compounds of formula (I) and pharmaceutically acceptable salts thereof can be administered as such, but it is usually preferred to administer them in the form of pharmaceutical compositions, which are used for animals and human beings.

It is preferred to employ the administration route which is the most effective for the treatment. For example, administration is made orally or non-orally by intrarectal, intraoral, subcutaneous, intramuscular or intravenous administration.

Examples of the forms for administration are capsules, tablets, granules, powders, syrups, emulsions, suppositories and injections.

Liquid compositions such as emulsions and syrups which are appropriate for oral administration can be prepared using water, sugars such as sucrose, sorbitol and fructose, glycols such as polyethylene glycol and propylene glycol, oils such as sesame oil, olive oil and soybean oil, preservatives such as benzoates, flavors such as strawberry flavor and peppermint, etc.

Capsules, tablets, powders and granules can be prepared using excipients such as lactose, glucose, sucrose and mannitol, disintegrating agents such as starch and sodium alginate, lubricants such as magnesium stearate and talc, binders such as polyvinyl alcohol, hydroxypropyl cellulose and gelatin, surfactants such as fatty acid esters, plasticizers such as glycerin, etc.

Compositions suitable for non-oral administration preferably comprise a sterilized aqueous preparation containing an active compound which is isotonic to the recipient's blood. For example, injections are prepared using a carrier which comprises a salt solution, a glucose solution, or a mixture of a salt solution and a glucose solution.

Compositions for topical application are prepared by dissolving or suspending an active compound in one or more kinds of solvents such as mineral oil, petroleum and polyhydric alcohol, or other bases used for topical drugs.

Compositions for intestinal administration are prepared using ordinary carriers such as cacao fat, hydrogenated fat and hydrogenated fat carboxylic acid, and are provided as suppositories.

The compositions for non-oral administration may additionally be formulated to contain one or more kinds of additives selected from glycols, oils, flavors, preservatives (including antioxidants), excipients, disintegrating agents, lubricants, binders, surfactants and plasticizers which are used for the preparation of compositions for oral administration.

The effective dose and the administration schedule for each of the compounds of formula (I) or a pharmaceutically acceptable salt thereof will vary depending on the administration route, the patient's age and body weight, and the type or degree of the diseases to be treated. However, it is generally appropriate to administer a compound of formula (I) or a pharmaceutically acceptable salt thereof in a dose of 0.01–1000 mg/adult/day, preferably 5–500 mg/adult/day, in one to several parts.

All the compounds of the present invention can be immediately applied to the treatment of kinase-dependent diseases of mammals as kinase inhibitors, specifically, those relating to tyrosine kinase. Specifically preferred are the compounds which have IC50 within the range of 10 nM–10 $\mu$M. Even more preferred are compounds which have IC50 within the range of 10 $\mu$M to −1 $\mu$M. Most preferred are compounds which have an IC50 value which is smaller than 1 $\mu$M.

Specific compounds of the present invention which have an activity to specifically inhibit one of the three types of protein kinase (for example, kinase which phosphorylates tyrosine, kinase which phosphorylates tyrosine and threonine, and kinase which phosphorylates threonine) can be selected. Tyrosine kinase-dependent diseases include hyperproliferative malfunction which is caused or maintained by abnormal tyrosine kinase activity. Examples thereof include psoriasis, pulmonary fibrosis, glomerulonephritis, cancer, atherosclerosis and anti-angiopoiesis (for example, tumor growth and diabetic retinopathy). Current knowledge of the relationship between other classes of kinase and specific diseases is insufficient. However, compounds having specific PTK-inhibiting activity have a useful treatment effect. Other classes of kinase have also been recognized in the same manner. Quercetin, genistein and staurosporin, which are all PTK-inhibitors, inhibit many kinds of protein kinase in addition to tyrosine kinase. However, as a result of their lack of the specificity, their cytotoxicity is high. Therefore, a PTK-inhibitor (or an inhibitor of other classes of kinase) which is apt to bring about undesirable side effects because of the lack of selectivity can be identified by the use of an ordinary test to measure cytotoxicity.

The present invention provides nitrogen-containing heterocyclic compounds and pharmaceutically acceptable salts thereof which inhibit phosphorylation of PDGF receptor to hinder abnormal cell growth and cell wandering and thus are useful for the prevention or treatment of cell-proliferative diseases such as arteriosclerosis, vascular reobstruction, cancer and glomerulosclerosis.

Although the present invention has been described in some detail by way of illustration for purposes of clarity of understanding, it will be apparent to those of ordinary skill in the art that various modifications and equivalents can be made without departing from the spirit and scope of the invention. It should be understood that the foregoing discussion and examples merely present a detailed description of certain preferred embodiments. All the patents, journal articles and other documents discussed or cited above are herein incorporated by reference in their entirety.

What is claimed is:

1. A compound selected from the group consisting of:

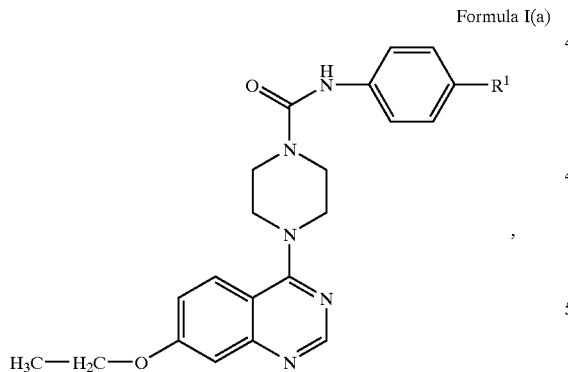

Formula I(a)

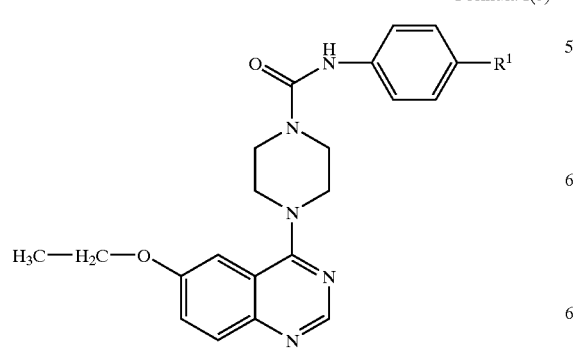

Formula I(b)

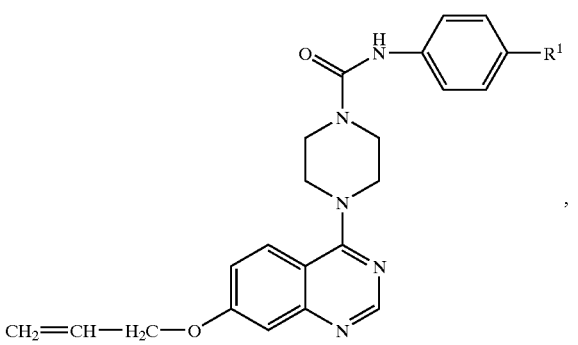

Formula I(c)

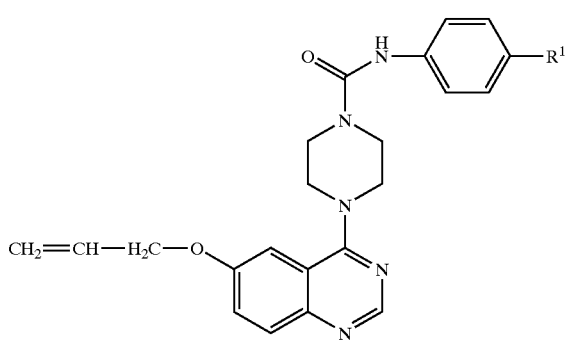

Formula I(d)

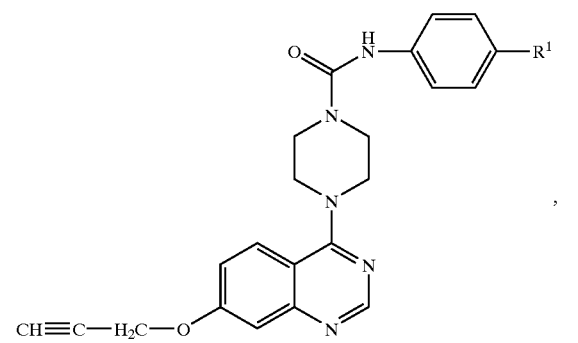

Formula I(e)

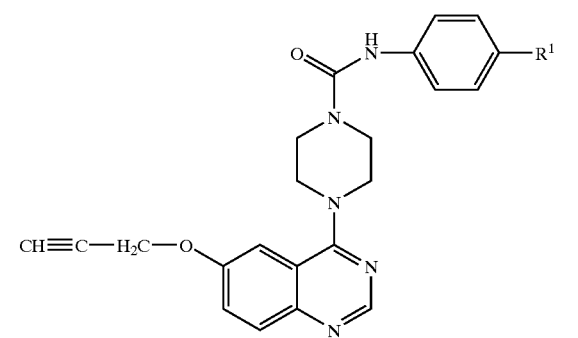

Formula I(f)

Formula I(g)

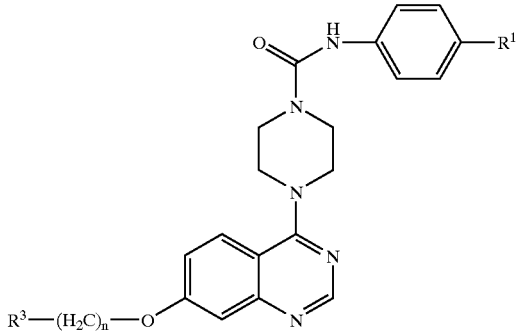

Formula I(h)

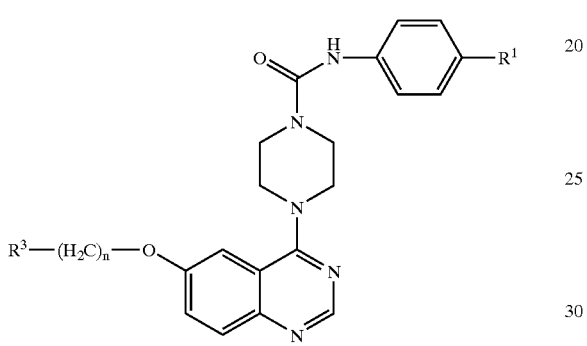

wherein when the compound is of Formula I(a) or I(b), $R^1$ is a member selected from the group consisting of: CN, O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy, 5-isoquinolyloxy, and position isomers and homologs thereof; and when the compound is of Formula I(c), I(d), I(e), I(f), I(g) or I(h), $R^1$ is a member selected from the group consisting of: CN, —O—$C_{1-8}$alkyl that is straight or branched chained, —O-phenyl, -naphthyloxy, indolyloxy and isoquinolinyloxy;

n is 1, 2 or 3;

$R^3$ is a member selected from the group consisting of: —OH, —O—$CH_3$, —O—$CH_2$—$CH_3$, —$NH_2$, —N(—$CH_3$)$_2$, —NH(—$CH_2$-phenyl), —NH(-Phenyl), —CN

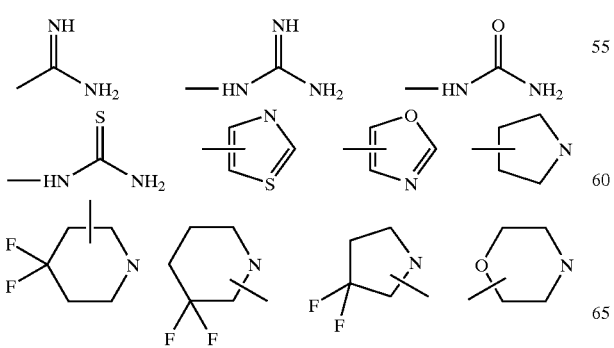

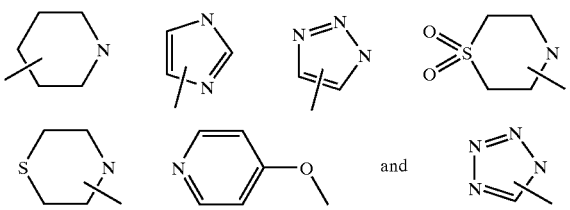 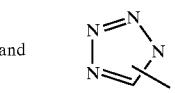 and and all pharmaceutically acceptable isomers, salts, hydrates, solvates and prodrug derivatives thereof.

2. The compound of claim 1, having Formula I(a) or Formula I(b):

Formula I(a)

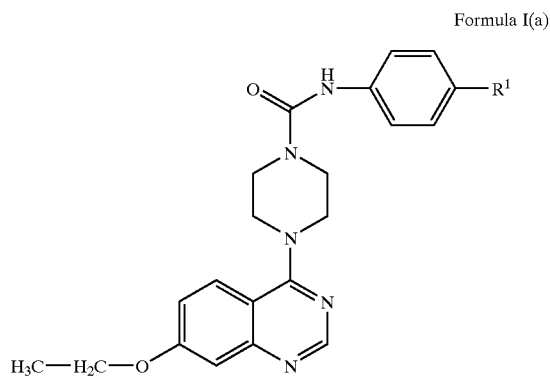

Formula I(b)

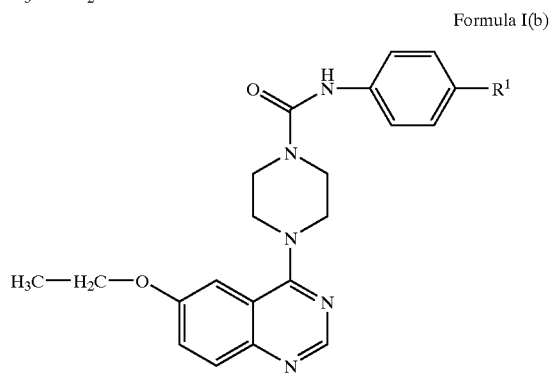

wherein $R^1$ is a member selected from the group consisting of: CN, O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy, 5-isoquinolyloxy, and position isomers and homologs thereof:

and all pharmaceutically acceptable isomers, salts, hydrates, solvates and prodrug derivatives thereof.

3. The compound of claim 1, having formula I(c) or formula I(d):

Formula I(c)

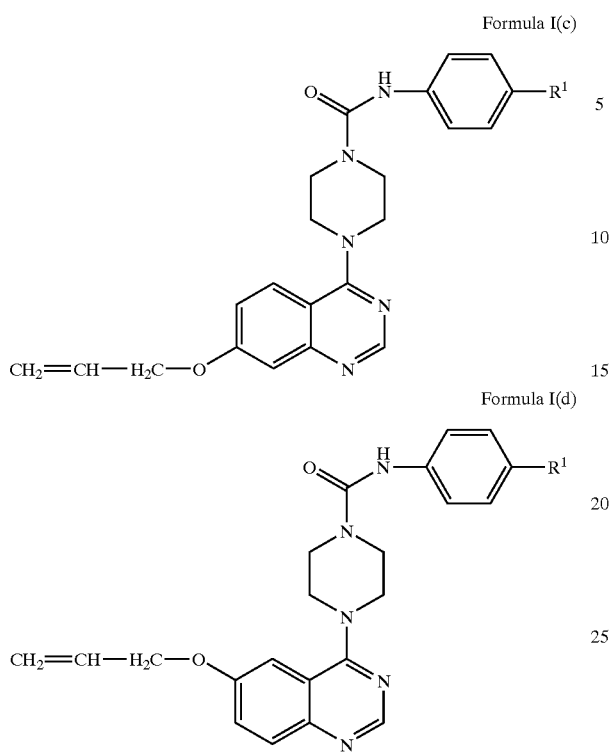

Formula I(d)

wherein

R¹ is a member selected from the group consisting of: CN, —O—$C_{1-8}$alkyl that is a straight or branched chained, —O-phenyl, naphthyloxy, indolyloxy and isoquinolinyloxy, and position isomers and homologs thereof, and all pharmaceutically acceptable isomers, salts, hydrates, solvates and prodrug derivatives thereof.

4. The compound of claim 3, wherein R¹ is a member selected from the group consisting of CN, —O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy, 5-isoquinolyloxy, and position isomers and homologs thereof;

and all pharmaceutically acceptable isomers, salts, hydrates, solvates and prodrug derivatives thereof.

5. The compound of claim 1, having formula I(e) or formula I(f):

Formula I(e)

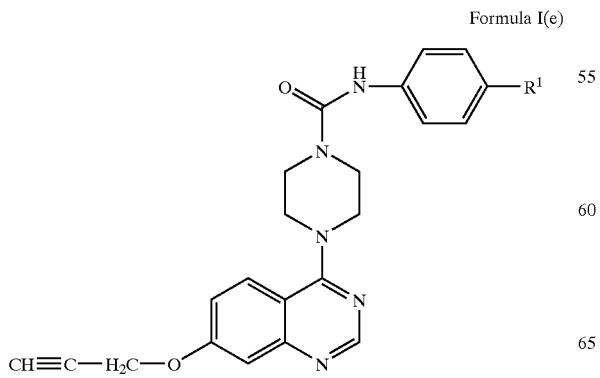

Formula I(f)

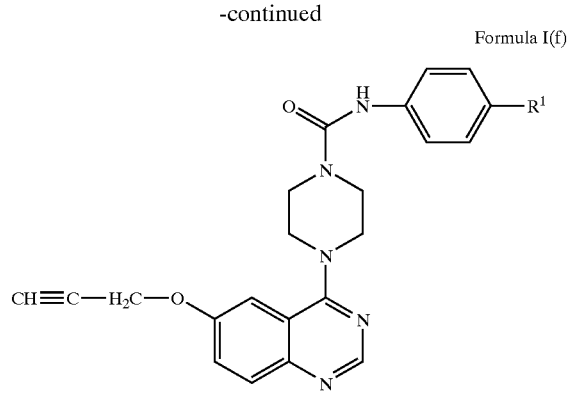

wherein

R¹ is a member selected from the group consisting of: CN, —O—$C_{1-8}$alkyl that is a straight or branched chained, —O-phenyl, naphthyloxy, indolyloxy and isoquinolinyloxy, and position isomers and homologs thereof, and all pharmaceutically acceptable isomers, salts, hydrates, solvates and prodrug derivatives thereof.

6. The compound of claim 5, wherein R¹ is a member selected from the group consisting of: CN, —O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy, 5-isoquinolyloxy, and position isomers and homologs thereof;

and all pharmaceutically acceptable isomers, salts, hydrates, solvates and prodrug derivatives thereof.

7. The compound of claim 1, having formula I(g) or formula I(h):

Formula I(g)

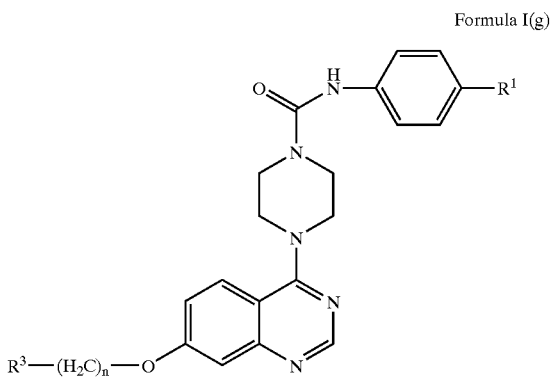

Formula I(h)

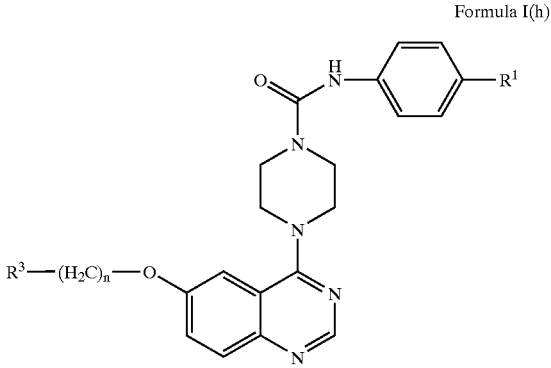

wherein n is 2 or 3;

R¹ is a member selected from the group consisting of: CN, —O—$C_{1-8}$alkyl that is a straight or branched chained, —O-phenyl, naphthyloxy, indolyloxy and isoquinoliniyloxy, and position isomers and homologs thereof, R₃ is a member selected from the group consisting of:
—OH, —O—CH₃, —O—CH₂—CH₃, —NH₂, —N(—CH₃)₂, —NH(—CH₂-phenyl), —NH(-Phenyl), —CN

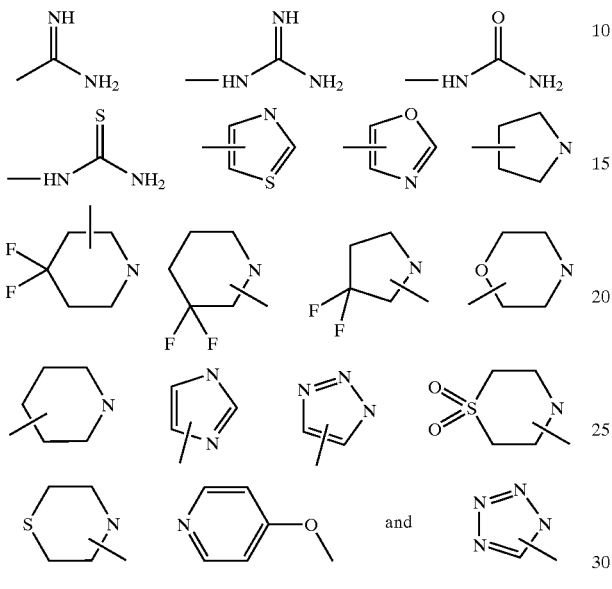

and all pharmaceutically acceptable isomers, salts, hydrates, solvates and prodrug derivatives thereof.

8. The compound of claim 7, wherein R¹ is a member selected from the group consisting of CN, —O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy, 5-isoquinolyloxy, and position isomers and homologs thereof;

and all pharmaceutically acceptable isomers, salts, hydrates, solvates and prodrug derivatives thereof.

9. A compound according to claim 1 selected from the group consisting of:

N-[4-(methylethoxy)phenyl]{4-[7-(2-morpholin-4-ylethoxy)quinazolin-4-yl]piperazinyl}carboxamide

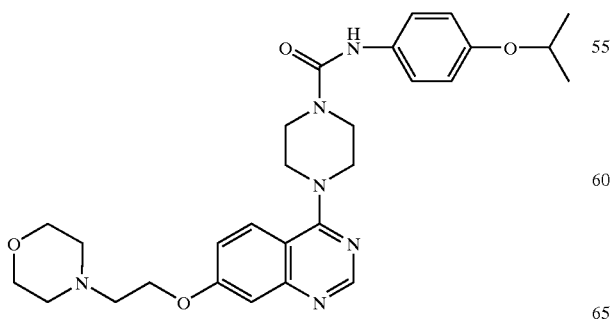

N-(4-cyanophenyl){4-[7-(2-morpholin-4-ylethoxy)quinazolin-4-yl]piperazinyl}carboxamide

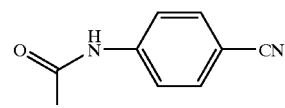

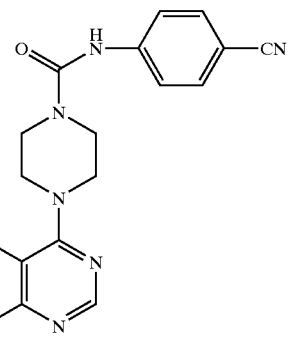

N-(4-cyanophenyl){4-[7-(2-pyrrolidinylethoxy)quinazolin-4-yl]piperazinyl}carboxamide N-[4-(methylethoxy)phenyl]{4-[7-(2-pyrrolidinylethoxy)quinazolin-4-yl]piperazinyl}carboxamide

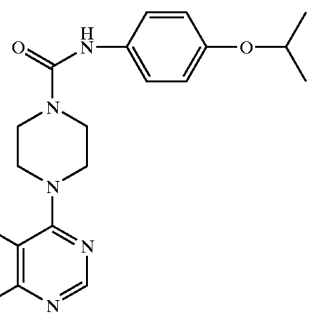

N-[4-(methylethoxy)phenyl]{4-[7-(2-piperidylethoxy)quinazolin-4-yl]piperazinyl}-carboxamide

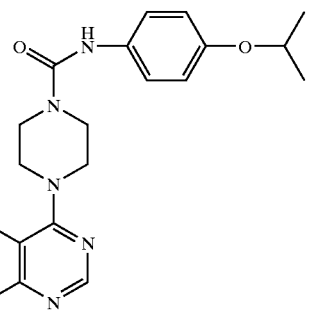

31

{4-[7-(2-methoxyethoxy)quinazolin-4-yl]piperazinyl}N-[4-(methylethoxy)phenyl]carboxamide

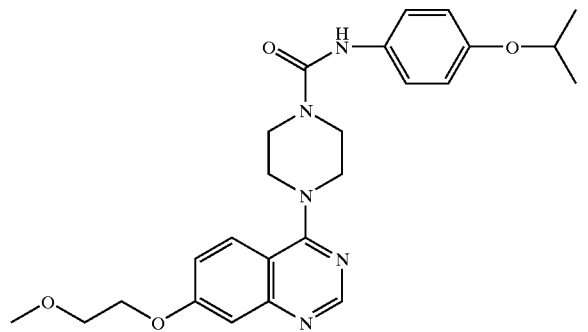

N-(4-cyanophenyl){4-[7-(2-methoxyethoxy)quinazolin-4-yl]piperazinyl}carboxamide

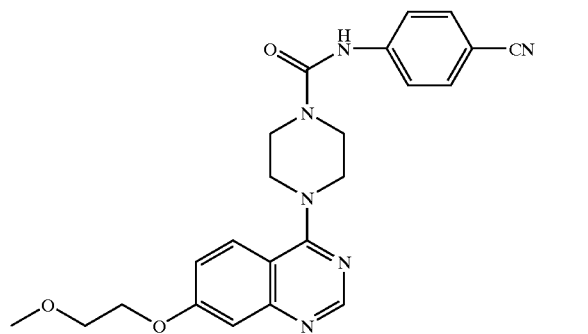

N-(4-cyanophenyl){4-[7-(2-piperidylethoxy)quinazolin-4-yl]piperazinyl}carboxamide

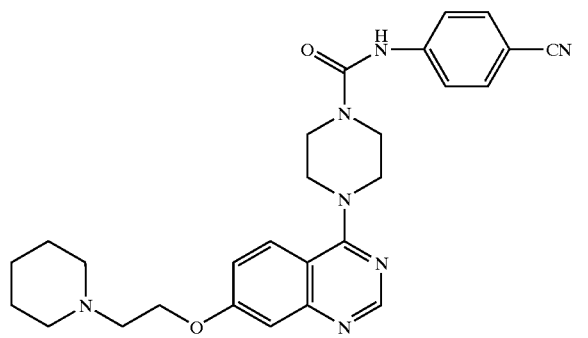

{4-[7-(2-methoxyethoxy)quinazolin-4-yl]piperazinyl}-N-(4-phenoxyphenyl)carboxamide

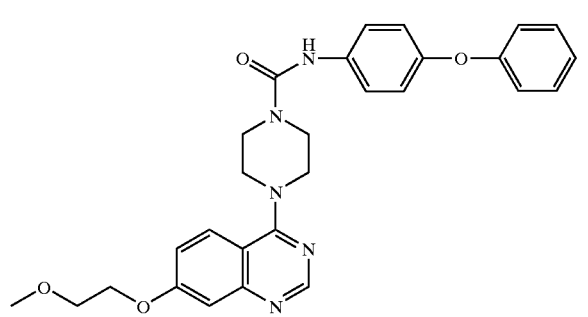

32

N-(4-indol-5-yloxyphenyl){4-[7-(2-methoxyethoxy)quinazolin-4-yl]piperazinyl}carboxamide

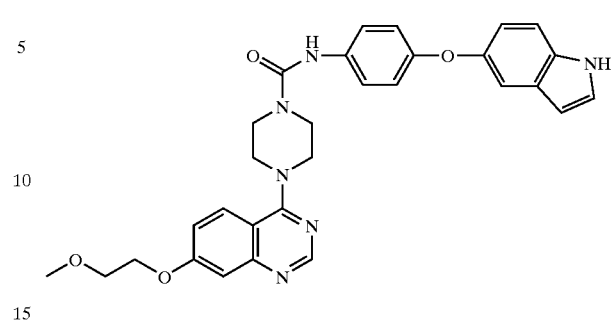

N-(4-(5-isoquinolyloxy)phenyl){4-[7-(2-methoxyethoxy)quinazolin-4-yl]piperazinyl}carboxamide

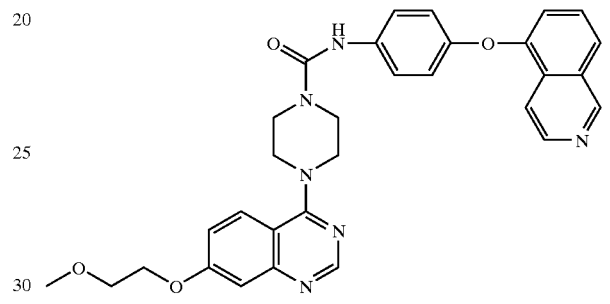

N-[4-(methylethoxy)phenyl]{4-[7-(3-piperidylpropoxy)quinazolin-4-yl]piperazinyl}-carboxamide

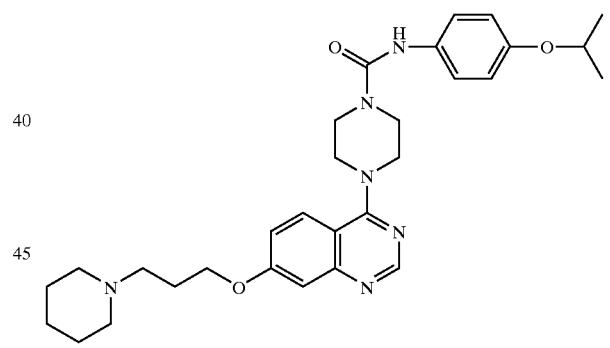

{4-[7-(2-methoxypropoxy)quinazolin-4-yl]piperazinyl}-N-(4-phenoxyphenyl)carboxamide

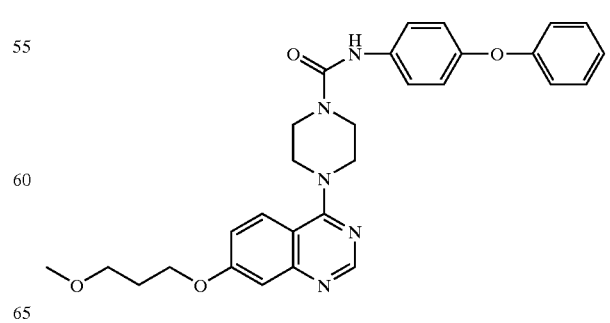

| 33 | 34 |
|---|---|
| N-(4-indol-5-yloxyphenyl){4-[7-(2-methoxypropoxy)quinazolin-4-yl]piperazinyl}carboxamide | N-(4-cyanophenyl){4-[7-(3-morpholin-4-ylpropoxy)quinazolin-4-yl]piperazinyl}carboxamide |

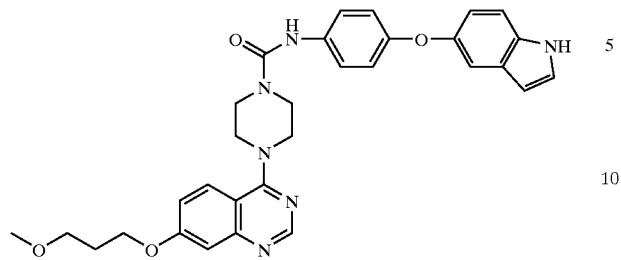

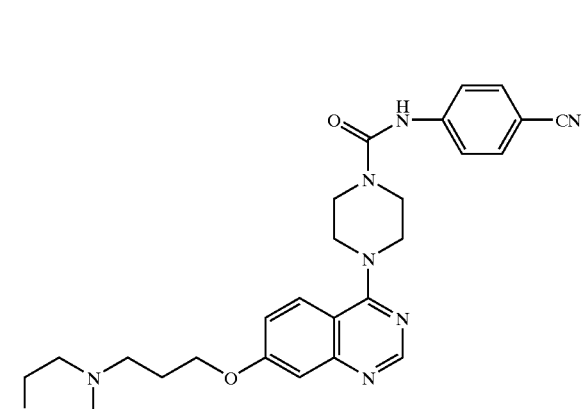

N-(4-(5-isoquinolyloxy)phenyl){4-[7-(2-methoxypropoxy)quinazolin-4-yl]piperazinyl}carboxamide

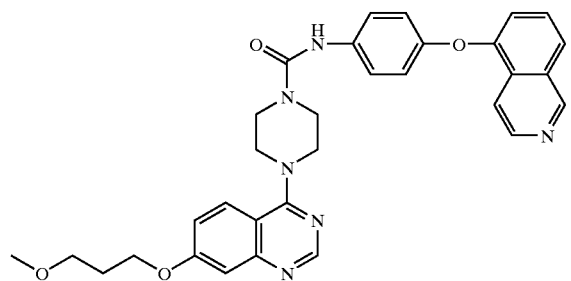

N-[4-(methylethoxy)phenyl]{4-[7-(3-pyrrolidinylpropoxy)quinazolin-4-yl]piperazinyl}carboxamide N-(4-cyanophenyl){4-[7-(3-piperidylpropoxy)quinazolin-4-yl]piperazinyl}carboxamide

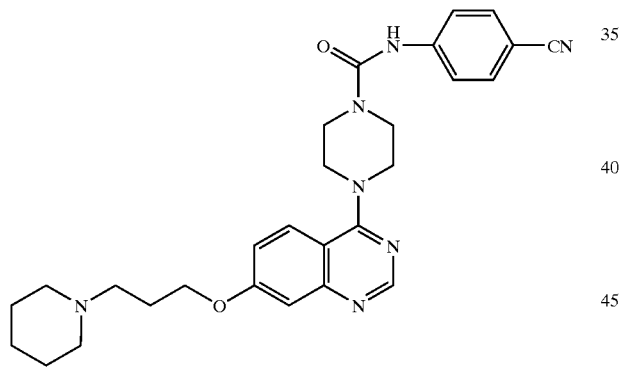

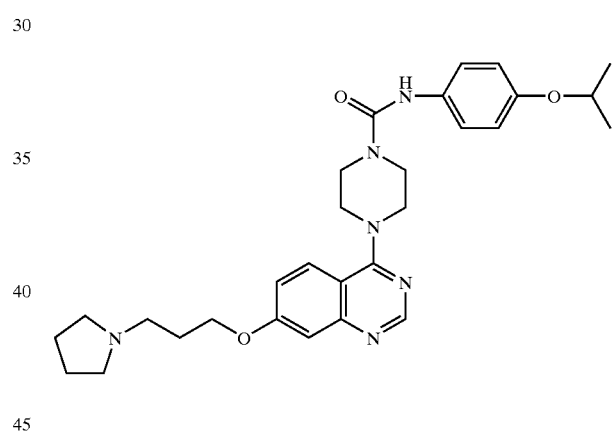

N-[4-(methylethoxy)phenyl]{4-[7-(3-morpholin-4-ylpropoxy)quinazolin-4-yl]piperazinyl}carboxamide N-(4-cyanophenyl){4-[7-(3-pyrrolidinylpropoxy)quinazolin-4-yl]piperazinyl}carboxamide

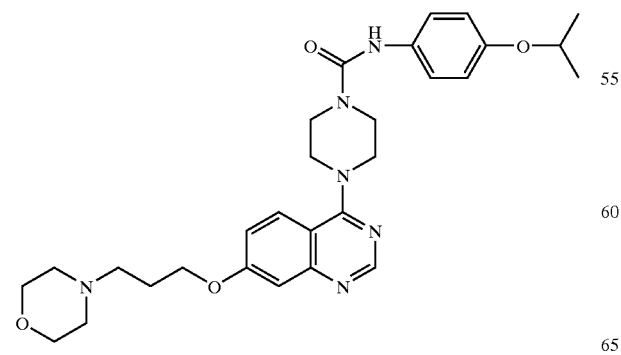

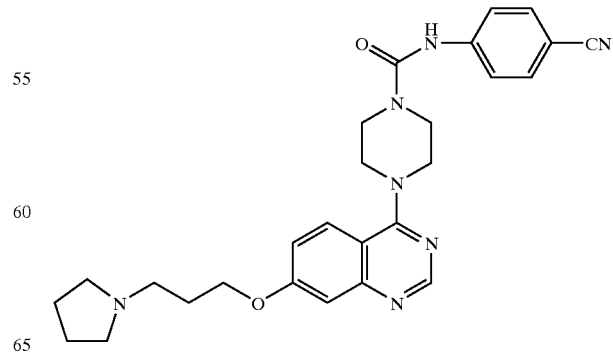

N-(4-cyanophenyl){4-[7-(3-methoxypropoxy)quinazolin-4-yl]piperazinyl}carboxamide

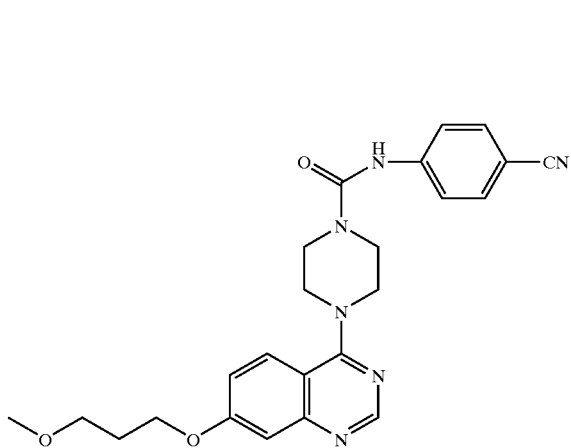

{4-[7-(3-methoxypropoxy)quinazolin-4-yl]piperazinyl}-N-[4-(methylethoxy)phenyl]carboxamide

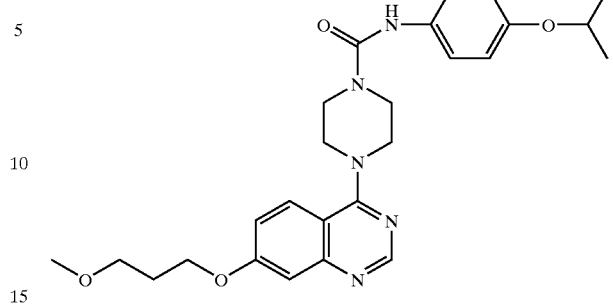

and all pharmaceutically acceptable isomers, salts, hydrates, solvates and prodrug derivatives thereof.

10. A pharmaceutical composition comprising an effective amount of a compound according to claim 1, or a pharmaceutically acceptable salt thereof, and a pharmaceutically acceptable diluent or carrier.

* * * * *